United States Patent [19]

Mandeville, III et al.

[11] Patent Number: 5,607,669
[45] Date of Patent: Mar. 4, 1997

[54] AMINE POLYMER SEQUESTRANT AND METHOD OF CHOLESTEROL DEPLETION

[75] Inventors: W. Harry Mandeville, III, Lynnfield; Stephen R. Holmes-Farley, Arlington, both of Mass.

[73] Assignee: GelTex Pharmaceuticals, Inc., Waltham, Mass.

[21] Appl. No.: 471,769

[22] Filed: Jun. 6, 1995

Related U.S. Application Data

[63] Continuation-in-part of Ser. No. 258,431, Jun. 10, 1994, and Ser. No. 332,096, Oct. 31, 1994.

[51] Int. Cl.⁶ .................................................. A61K 31/785
[52] U.S. Cl. ...................... 424/78.12; 424/45; 424/451; 424/456; 424/489; 424/464; 424/439; 424/442; 514/824
[58] Field of Search .................... 424/78.12, 486, 424/497; 514/824, 740; 525/328.2, 379

[56] References Cited

U.S. PATENT DOCUMENTS

| | | | |
|---|---|---|---|
| 3,288,770 | 11/1966 | Butler . | |
| 3,308,020 | 3/1967 | Wolf et al. | 167/65 |
| 3,383,281 | 5/1968 | Wolf et al. | 167/65 |
| 3,692,895 | 9/1972 | Nelson et al. . | |
| 3,780,171 | 12/1973 | Irmscher et al. . | |
| 3,787,474 | 1/1974 | Daniels et al. . | |
| 3,803,237 | 4/1974 | Lednicer et al. | 260/584 R |
| 3,980,770 | 9/1976 | Ingelman et al. . | |
| 4,027,009 | 5/1977 | Grier et al. . | |
| 4,071,478 | 1/1978 | Shen et al. . | |
| 4,098,726 | 7/1978 | Wagner et al. | 528/403 |
| 4,101,461 | 7/1978 | Strop et al. . | |
| 4,111,859 | 9/1978 | Strop et al. . | |
| 4,205,064 | 5/1980 | Wagner et al. | 424/78 |
| 4,217,429 | 8/1980 | Wagner et al. | 525/411 |
| 4,340,585 | 7/1982 | Borzatta et al. | 424/79 |
| 4,540,760 | 9/1985 | Harada et al. . | |
| 4,557,930 | 12/1985 | Kihara et al. | 424/79 |
| 4,559,391 | 12/1985 | Ueda et al. . | |
| 4,605,701 | 8/1986 | Harada et al. . | |
| 4,680,360 | 7/1987 | Ueda et al. . | |
| 4,759,923 | 7/1988 | Buntin et al. | 424/440 |
| 5,055,197 | 10/1991 | Albright et al. | 210/638 |
| 5,236,701 | 8/1993 | St. Pierre et al. | 424/78 |
| 5,374,422 | 12/1994 | St. Pierre et al. . | |
| 5,430,110 | 7/1995 | Ahlers et al. . | |
| 5,451,397 | 9/1995 | Albright et al. . | |
| 5,462,730 | 10/1995 | McTaggart et al. | 424/78.35 |

FOREIGN PATENT DOCUMENTS

| | | |
|---|---|---|
| 0162388 | 11/1985 | European Pat. Off. . |
| 0373852A2 | 6/1990 | European Pat. Off. . |
| 0432995A1 | 6/1991 | European Pat. Off. . |
| 0459632A1 | 12/1991 | European Pat. Off. . |
| 929391 | 6/1963 | United Kingdom . |
| 1567294 | 5/1980 | United Kingdom . |
| WO91/18027 | 11/1991 | WIPO . |
| WO92/10522 | 6/1992 | WIPO . |
| WO94/04596 | 3/1994 | WIPO . |
| WO94/27620 | 12/1994 | WIPO . |

OTHER PUBLICATIONS

Heming, A. E. and Flanagan, Thomas L., "Considerations in the Selection of Cation Exchange Resins for Therapeutic Use," *Annals of the New York Academy of Sciences*, 57:239–251 (1954).

McCarthy, Peter A., "New Approaches to Atherosclerosis: An Overview," *Medicinal Research Reviews*, 13(2):139–159 (1993).

*Primary Examiner*—Charles T. Jordan
*Assistant Examiner*—John R. Hardee
*Attorney, Agent, or Firm*—Hamilton, Brook, Smith & Reynolds, P.C.

[57] ABSTRACT

An amine polymer includes first and second substituents bound to amines of the polymer. The first substituent includes a hydrophobic moiety. The second substituent includes a quaternary amine-containing moiety. A method for binding bile salts of bile acids in a mammal includes orally administering to the mammal a therapeutically-effective amount of the amine polymer.

25 Claims, 8 Drawing Sheets

AMINE POLYMER SEQUESTRANT AND METHOD OF CHOLESTEROL DEPLETION

Related Applications

This is a Continuation-in-Part of application Ser. No. 08/258,431, filed Jun. 10, 1994, and of application Ser. No. 08/332,096, filed Oct. 31, 1994, the teachings of both of which are incorporated herein in their entirety.

BACKGROUND OF THE INVENTION

Salts of bile acids act as detergents to solubilize and consequently aid in digestion of dietary fats. Bile acids are precursors to bile salts, and are derived from cholesterol. Following digestion, bile acids can be passively absorbed in the jejunum, or, in the case of conjugated primary bile acids, reabsorbed by active transport in the ileum. Bile acids which are not reabsorbed are deconjugated and dehydroxylated by bacterial action in the distal ileum and large intestine.

Reabsorption of bile acids from the intestine conserves lipoprotein cholesterol in the bloodstream. Conversely, blood cholesterol level can be diminished by reducing reabsorption of bile acids.

One method of reducing the amount of bile acids that are reabsorbed is oral administration of compounds that sequester the bile acids and cannot themselves be absorbed. The sequestered bile acids are consequently excreted.

Many bile acid sequestrants, however, do not bind conjugated primary bile acids, such as conjugated cholic and chenodeoxycholic acids well enough to prevent substantial portions from being reabsorbed. In addition, the volume of sequestrants that can be ingested safely is limited. As a result, the effectiveness of sequestrants to diminish blood cholesterol levels is also limited.

A need exists, therefore, for a sequestrant and a method which overcomes or minimizes the referenced problems.

SUMMARY OF THE INVENTION

The present invention relates to amine polymer sequestrants and to a method for binding salts of bile acids in a mammal.

The amine polymer includes a first substituent, bound to an amine of the amine polymer, that includes a hydrophobic moiety. A second substituent, bound to an amine of the amine polymer, includes a quaternary amine-containing moiety.

The method includes orally administering to a mammal a therapeutic amount of an amine polymer having a first substituent, bound to an amine of the amine polymer, that includes a hydrophobic moiety, and a second substituent, bound to an amine of the amine polymer, that includes a quaternary amine-containing moiety.

This invention has many advantages. For example, the amine polymer of the invention binds conjugated primary bile acids that would otherwise be reabsorbed by active transport. Additionally, the sequestration of primary bile acids by the amine polymer is essentially irreversible in the intestine, as evidenced by the fact that bacterial deconjugation and dehydroxylation of bound bile acids is substantially prevented. Consequently, the effectiveness of a given dosage of sequestrant to diminish plasma lipid levels is significantly increased. Other, specific advantages include reduced hepatic and aortic lipid levels and enhanced antiatherosclerotic activity.

DETAILED DESCRIPTION OF THE INVENTION

Figure 1:
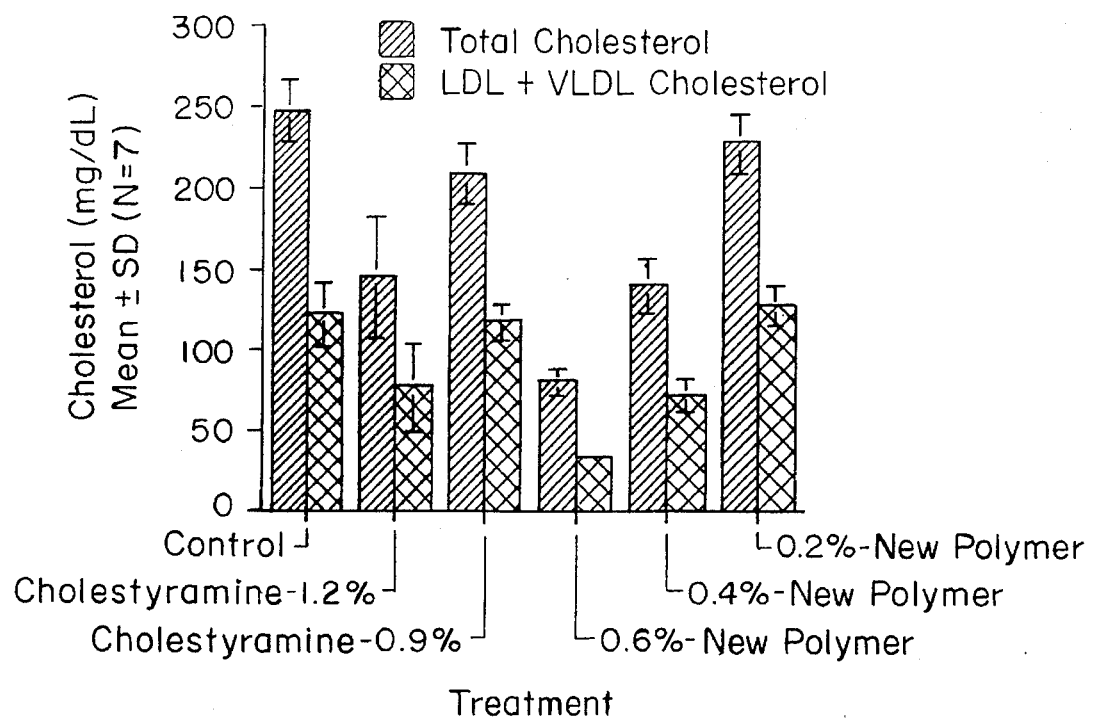
FIG. 1 is a bar graph of the comparative effect of bile acid sequestrants on plasma cholesterol in male hamsters fed a high fat diet for 14 weeks.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Generally, the amine polymers of the invention include distinct first and second substituents. The first substituent is bound to an amine of the amine polymer and includes a hydrophobic moiety. The second substituent is bound to an amine of the amine polymer and includes a quaternary amine-containing moiety. It is to be understood that the first and second substituents can be bound to the same amine and/or different amines of the amine polymer. The amine polymers of the invention are particularly suitable for binding conjugated primary bile acids, such as cholic and chenodeoxycholic acids, in mammals by oral administration of the polymer. A particularly suitable form for oral administration of the amine polymer is that which will form a gel in the stomach of a patient.

Examples of suitable methods by which the amine polymer of the invention can be formed are shown below:

1. One method involves polymerization of an amine monomer to form a homopolymer. Examples of this method include polymerization of allylamine, ethyleneimine, vinylamine, 1,2-diaminoethene, aminoethylacrylamide, aminopropylacrylate, or p-aminomethylstyrene, to form their respective homopolymers.

2. Another method involves copolymerizing an amine monomer with one or more additional monomers. These additional monomers include amine monomers, such as those listed above, and non-amine monomers, such as acrylamide, styrene, divinylbenzene, vinyl alcohol, or vinyl chloride. Examples include copoly(allylamine/acrylamide), copoly(vinylamine/allylamine), copoly(amino-ethylacrylamide/acrylamide), and copoly(allylamine/divinylbenzene).

3. Still another method involves polymerization of a non-amine monomer to form a homopolymer that is subsequently chemically modified to form an amino polymer. Examples of this method include polymerization of vinyl formamide, vinyl acetamide, vinyl chloride, vinyl bromide, allyl chloride, allyl bromide, acrylamide, or acrylonitrile, to form their respective homopolymers. Each homopolymer would then be chemically altered to form an amine polymer using such reactions as hydrolysis, nucleophilic substitution, or reduction. The first four homopolymers listed above would then become poly(vinylamine) and the last four would become poly(allylamine). It is to be understood that not all of the initial non-amine monomer need be chemically altered, resulting in an amine polymer that contains some of the initial non-amine monomers in a non-amine state.

4. A fourth method involves copolymerizing a non-amine monomer with one or more additional monomers. These additional monomers could include amine monomers, such as those listed in the first method, and non-amine monomers, such as those listed in the third method. The resulting copolymer would then be chemically altered to form an amine polymer as in the third method. Examples would include copolymerization of acrylamide and styrene, followed by reduction to form copoly(allylamine/styrene), copolymerization of acrylonitrile and vinyl formamide, followed by reduction and hydrolysis, to form copoly(allylamine/vinylamine), and copolymerization of acrylonitrile and allylamine, followed by reduction, to form poly(allylamine). It is to be understood that not all of the initial non-amine monomer be chemically altered, resulting in an amine polymer that contains some of the initial non-amine monomers in a non-amine state.

5. A fifth method involves forming an amine polymer through a condensation mechanism. Examples of this method would include reaction of diethylenetriamine and epichlorohydrin, 1,3-dibromopropane and ethylenediamine, spermine and 1,4-butanediol diglycidyl ether, or tris(2-aminoethyl)amine and 1,10-dibromodecane.

Each of these amine polymers typically has a molecular weight greater than 2,000. Examples of resulting suitable amine polymers include poly(vinylamine), poly(allylamine), and poly(ethyleneimine). A preferred amine polymer is poly(allylamine).

Preferably, the amine polymer is crosslinked, such as by reacting the polymer with a suitable crosslinking agent. Examples of suitable crosslinking agents include acryloyl chloride, epichlorohydrin, butanedioldiglycidyl ether, ethanedioldiglycidyl ether, dimethyl succinate, etc. Epichlorohydrin is a preferred crosslinking agent. Typically, the amount of crosslinking agent that is reacted with the amine polymer is sufficient to cause between about 0.5 and twenty percent of the amines available for reaction to react with the crosslinking agent. In a preferred embodiment, between about 0.5 and six percent of the amine groups react with the crosslinking agent.

Crosslinking of the polymer can be achieved by reacting the polymer with a suitable crosslinking agent in an aqueous caustic solution at about 25° C. for a period of time of about eighteen hours to thereby form a gel. The gel is then combined with water or dried to form a particulate solid. The particulate solid can then be washed with water and dried under suitable conditions, such as a temperature of about 50° C. for a period of time of about eighteen hours.

The amine polymer can then be alkylated. Generally, at least two distinct alkylating agents are employed to alkylate the amine polymer. An "alkylating agent," as that term is employed herein, means a reactant that, when reacted with a crosslinked polymer, causes a substituted or unsubstituted alkyl group or derivative thereof (e.g., an aralkyl, hydroxyalkyl, alkylammonium salt, alkylamide, or combination thereof) to be covalently bound to one or more of the nitrogen atoms of the polymer.

At least one alkylating agent is employed to react with the amine polymer to form a first substituent on the amine polymer. The first substituent is bound to an amine of the amine polymer, and includes a hydrophobic moiety. Examples of suitable hydrophobic moieties are those which include alkyl groups of at least six carbons. In one embodiment, the hydrophobic moiety includes an alkyl group of between about eight and twelve carbons. Preferably, the hydrophobic moiety includes an alkyl group of about ten carbons. Specific examples of suitable hydrophobic moieties include alkyl halides, such as n-hexyl halide, n-octyl halide, n-decyl halide, n-dodecyl halide, n-tetradecyl halide, n-octadecyl halide, and combinations thereof. Other examples include: a dihaloalkane that includes an alkyl group of at least six carbons (e.g., a 1,10-dihalodecane); an hydroxyalkyl halide (e.g., an 11-halo-1-undecanol); an aralkyl halide (e.g., a benzyl halide); etc. A preferred halogen component of the alkyl halides is bromine. An example of a particularly preferred alkylating agent which, when reacted with the amine polymer, will cause formation of an amine polymer reaction product that includes a first substituent, is 1-bromodecane.

The amine polymer is also alkylated with a second alkylating agent. The second alkylating agent, when reacted with the amine polymer, will result in an amine polymer reaction product that includes a second substituent that is bound to an amine of the amine polymer. The second substituent includes a quaternary amine-containing moiety. In one embodiment, the quaternary amine-containing moiety of the second substituent includes an alkyl trimethylammonium, wherein the alkyl component includes between about two and twelve carbons. Examples of preferred alkyl groups of the alkyl trimethylammonium are hexyl, octyl, and decyl groups. Examples of suitable second alkylating agents include alkyl halide trimethylammonium salts, such as (4-halobutyl) trimethylammonium salt, (6-halohexyl)trimethylammonium salt, (8-halooctyl)trimethylammonium salt, (10-halodecyl) trimethylammonium salt, (12-halododecyl)trimethylammonium salt, and combinations thereof. A particularly preferred second alkylating agent is (6-bromohexyl)trimethylammonium bromide.

In one embodiment, a suitable (6-bromohexyl) trimethylammonium bromide can be formed by adding to a 5 L, three-neck flask, equipped with a mechanical stirrer, thermometer, and a condenser at −5° C., tetrahydrofuran (3.0 L) and 1,6-dibromohexane (1.0 kg). To this mixture is added trimethylamine (gas; 241.5 grams) over a 1 hour period. At the end of this addition the temperature is ~40° C. The mixture is stirred and temperature maintained at 40° C. for 24 hours. The solid is then filtered off and rinsed with tetrahydrofuran (2.0 L). The solid is dried in a vacuum oven to yield 1070.2 grams of white solid.

The amine polymer is typically alkylated by combining the polymer with the alkylating agents, simultaneously or sequentially in any order, in an organic solvent. The amount of each of the first and second alkylating agents combined with the amine polymer is generally sufficient to cause reaction of each of the alkylating agents with between about five and ninety-five percent of amine groups on the amine polymer. Preferably the range is between about ten and ninety percent. In a particularly preferred embodiment, the range is between about thirty and seventy percent. Examples of suitable organic solvents include methanol, ethanol, acetonitrile, etc. A preferred organic solvent is methanol.

In one embodiment, the reaction mixture is heated over a period of about forty minutes to a temperature of about 65° C., with stirring. Typically, an aqueous sodium hydroxide solution is intermittently added during the reaction period. Preferably, the reaction period at 65° C. is about eighteen hours, followed by gradual cooling to a room temperature of about 25° C. over a period of about four hours. The resulting reaction product is then filtered, resuspended in methanol, filtered again, and then washed with a suitable aqueous solution, such as two molar sodium chloride, and then with deionized water. The resultant solid product is then dried under suitable conditions, such as at a temperature of about 60° C. in a forced-air oven. The dried solid can then be subsequently processed. Preferably, the solid is ground and passed through an 80 mesh sieve.

In a particularly preferred embodiment of the invention, the amine polymer is a crosslinked poly(allylamine), wherein the first substituent includes a hydrophobic decyl moiety, and the second amine substituent includes a hexyltrimethylammonium. Further, the particularly preferred crosslinked poly(allylamine) is crosslinked by epichlorohydrin that is present in a range of between about two and six percent of the amines of the polymer.

The amine polymer of the invention can be subsequently treated or combined with other materials to form a composition for oral administration of the amine polymer.

The present pharmaceutical compositions are generally prepared by known procedures using well known and readily available ingredients. In making the compositions of the present invention, the amine polymer can be present alone, can by admixed with a carrier, diluted by a carrier, or enclosed within a carrier which may be in the form of a capsule, sachet, paper or other container. When the carrier serves as a diluent, it can be a solid, semi-solid or liquid material which acts as a vehicle, excipient or medium for the polymer. Thus, the compositions can be in the form of tablets, pills, powders, lozenges, sachets, cachets, elixirs, suspensions, syrups, aerosols, (as a solid or in a liquid medium), soft or hard gelatin capsules, sterile packaged powders, and the like. Examples of suitable carrier, excipients, and diluents include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, propylhydroxybenzoates, and talc.

A negatively charged counterion of the pharmaceutical composition can include organic ions, inorganic ions, or combinations thereof. Inorganic ions suitable for use in this invention include halide (especially chloride), phosphate, carbonate, bicarbonate, and sulfate. Suitable organics ions include acetate, ascorbate, benzoate, citrate, dihydrogen citrate, hydrogen citrate, oxalate, succinate, and tartrate.

In a preferred embodiment, the counterion does not have a detrimental side effect to the patient but rather is selected to have a therapeutic or nutritional benefit to the patient.

The method of the invention includes administering to a mammal, such as by oral administration, a therapeutic amount of the amine polymer having a first substituent, bound to an amine of the amine polymer, that includes a hydrophobic moiety, and a second substituent, bound to an amine of the amine polymer, that includes a quaternary amine-containing moiety. Generally, a therapeutic amount of the amine polymer is an amount of the amine polymer in a range of between about 0.1 grams/day and about 10 grams/day.

In one embodiment, the method of the invention is a method for binding bile salts in a mammal, comprising the step of orally administering to the mammal a therapeutic amount of the amine polymer of the invention. In another embodiment, the invention is a method for reducing blood cholesterol in a mammal, comprising the step of administering to the mammal a therapeutic amount of the amine polymer of the invention. In still another embodiment, the invention includes a method for treating atherosclerosis in a mammal, comprising the step of administering to the mammal a therapeutic amount of the amine polymer of the invention. In still another embodiment, the method of the invention is that of treating hypercholesterolemia in a mammal, comprising the step of administering to the mammal a therapeutic amount of the amine polymer of the invention.

Another embodiment of the invention is a method for reducing plasma lipid content of a mammal, comprising the step of orally administering the amine polymer of the invention to tightly sequester conjugated primary bile acids secreted by the mammal, whereby a substantial portion of the conjugated primary bile acids are excreted by the mammal, thereby causing accelerated lipid metabolization and consequent lowering of plasma lipid content of the mammal. In a preferred embodiment, the sequestered conjugated primary bile acids include conjugated cholic acid and conjugate chenodeoxycholic acid.

The teachings of U.S. patent application Ser. No. 08/469, 659 entitled "Hydrophobic Amine Polymer Sequestrant and Method Cholesterol Depletion," filed on Jun. 6, 1995 by Mandeville et al., are incorporated herein by reference in their entirety.

The invention will now be further and specifically described by the following examples. All parts and percentages are by weight unless otherwise specified.

Exemplification

EXAMPLE 1

Preparation of a Poly (allylamine) Hydrochloride

To a 2 liter, water-jacketed reaction kettle equipped with (1) a condenser topped with a nitrogen gas inlet, (2) a thermometer, and (3) a mechanical stirrer was added concentrated hydrochloric acid (360 mL). The acid was cooled to 5° C. using circulating water in the jacket of the reaction kettle (water temperature=0° C.). Allylamine (328.5 mL, 250 grams) was added dropwise with stirring while maintaining the reaction temperature at 5°–10° C. After addition was complete, the mixture was removed, placed in a 3 liter one-neck flask, and 206 grams of liquid was removed by rotary vacuum evaporation at 60° C. Water (20 mL) was then added and the liquid was returned to the reaction kettle. Azobis(amidinopropane) dihydrochloride (0.5 grams) suspended in 11 mL of water was then added. The resulting reaction mixture was heated to 50° C. under a nitrogen atmosphere with stirring for 24 hours. Additional axobis(amidinopropane) dihydrochloride (0.5 grams) suspended in 11 mL of water was then added, after which heating and stirring were continued for an additional 44 hours.

At the end of this period, distilled water (100 mL) was added to the reaction mixture and the liquid mixture allowed to cool with stirring. The mixture was then removed and placed in a 2 liter separatory funnel, after which it was added dropwise to a stirring solution of methanol (4 L), causing a solid to form. The solid was removed by filtration, resuspended in methanol (4 L), stirred for 1 hour, and collected by filtration. The methanol rinse was then repeated one more time and the solid dried in a vacuum oven to afford 215.1 grams of poly(allylamine) hydrochloride as a granular white solid.

EXAMPLE 2

Preparation of Poly(allylamine) Hydrochloride Crosslinked With Epichlorohydrin

To a 5 gal vessel was added poly(allylamine) hydrochloride prepared as described in Example 1 (1 kg) and water (4 L). The mixture was stirred to dissolve the hydrochloride and the pH was adjusted by adding solid NaOH (284 grams). The resulting solution was cooled to room temperature, after which epichlorohydrin crosslinking agent (50 mL) was added all at once with stirring. The resulting mixture was stirred gently until it gelled (about 35 minutes). The crosslinking reaction was allowed to proceed for an additional 18 hours at room temperature, after which the polymer gel was removed and placed in portions in a blender with a total of 10 L of water. Each portion was blended gently for about 3 minutes to form coarse particles which were then stirred for 1 hour and collected by filtration. The solid was rinsed three times by suspending it in water (10 L, 15 L, 20 L), stirring each suspension for 1 hour, and collecting the solid each time by filtration. The resulting solid was then rinsed once by suspending it in isopropanol (17 L), stirring the mixture for 1 hour, and then collecting the solid by filtration, after which the solid was dried in a vacuum over at 50° C. for 18 hours to yield about 677 grams of the crosslinked polymer as a granular, brittle, white solid.

EXAMPLE 3

Alkylation of Six Percent Crosslinked Amine Polymer

Crosslinked poly(allylamine) was made as stated in Example 2. To a large flask were added the crosslinked poly(allylamine) (300 grams; ground to ~30 mesh), (6-bromohexyl)trimethylammonium bromide (316.4 grams), 1-bromodecane (188.9 grams), and methanol (8 L). The mixture was heated to 65° C. with stirring. Upon reaching 65° C. (~40 minutes), aqueous sodium hydroxide (44.9 grams of 50% solution) was added and the stirring continued at 65° C. for 2 hours. Two additional aliquots of aqueous sodium hydroxide (44.9 grams of 50% solution each) were sequentially added and the stirring continued at 65° C. for an additional 2 hours for each aliquot. A final aliquot of aqueous sodium hydroxide (44.9 grams of 50% solution) was then added and the stirring continued at 65° C. for an additional 12 hours. The mixture was then allowed to cool to room temperature (~4 hours).

The solid product was filtered off and resuspended in methanol such that the conductivity was less than 2.5 mS/cm (~20L). The mixture was stirred for 30 minutes and the solid filtered off. The solid was then washed by suspension, stirring for 30 minutes, and filtration, from the following fluids:

1. 11 L 2 M NaCl (aqueous)
2. 11 L 2 M NaCl (aqueous)
3. 8 L deionized water
4. 8 L deionized water
5. 8 L deionized water The solid was then dried in a 60° C. forced air drying oven to yield 450 grams of an off-white solid. The solid was then ground and passed through an 80 mesh sieve. The resulting polymer is hereinafter referred to as "Example 3 polymer.")

EXAMPLE 4

Alkylation of Crosslinked Amine Polymer

The procedure for Example 3 was repeated using different amounts of reagents. All amounts, times and procedures were unchanged except:

570 grams (6-bromohexyl)trimethylammonium bromide
390 grams 1-bromodecane
80.1 grams aqueous sodium hydroxide in each addition
16.5 L 2M NaCl (aqueous) in each wash
9 L deionized water in each wash The yield of this reaction was: 684.6 grams of an off-white solid.

EXAMPLE 5

Alkylation of Three Percent Crosslinked Amine Polymer

Crosslinked poly(allylamine) was made by the same method described in Example 2 except that the level of epichlorohydrin was 25 mL instead of 50 mL, resulting in 3% crosslinked poly(alkylamine). The procedure of Example 3 was then repeated using different amounts of reagents. All amounts, times, and procedures were unchanged except:

300 grams of Poly(allylamine) crosslinked at 3%, −30 mesh size
636 grams (6-bromohexyl)trimethylammonium bromide
435 grams 1-bromodecane
88.7 grams aqueous sodium hydroxide in each addition
18.4 L 2M NaCl (aqueous) in each wash
10 L deionized water in each wash

EXAMPLE 6

To a 12-1 round bottom flask equipped with a mechanical stirrer, a thermometer, and a condenser was added methanol (5 L) and sodium hydroxide (133.7 grams). The mixture was stirred until the solid was dissolved and crosslinked poly-(allylamine) (from Example 2; 297 grams; ground to −80 mesh size) was added along with additional methanol (3 L). (6-Bromohexyl)trimethylammonium bromide (522.1 grams) and 1-bromodecane (311.7 grams) were added and the mixture heated to 65° C. with stirring. After 18 hours at 65° C. the mixture was allowed to cool to room temperature. The solid was filtered off and rinsed by suspending, stirring for 30 minutes, and filtering off the solid from:

1. Methanol, 12 L
2. Methanol, 12 L 3. 2M Aqueous NaCl 22 L
4. 2M Aqueous NaCl 22 L
5. Deionized Water 22 L
6. Deionized Water 22 L
7. Deionized Water 22 L
8. Isopropanol 22 L The solid was dried in a vacuum oven at 50° C. to yield 505.1 grams of off-white solid. The solid was then ground to pass through an 80 mesh sieve.

EXAMPLE 7

Experimental Procedures and Results
Experimental Procedures

Eight week old, male golden Syrian hamsters are housed in individual hanging stainless steel cages. The animals were allowed to acclimate for one week, then placed on laboratory chow supplemented with 5.5% coconut oil, 4.5% corn oil and 0.1% cholesterol. The chow diet contains 3–5% endogenous fat resulting in a total fat content of 13–15% (28.6–33% of calories). Bile acid sequestrants formed by the procedure described in Example 6, above, were mixed into the diet of the test groups at initiation of the high fat diet. Control animals were fed only the fat containing diet. Baseline and 5 week blood samples were drawn from the retroorbital sinus after anesthesia with a 50% $CO_2:O_2$ gas mixture. Plasma cholesterol levels were measured on a Technicon Autoanalyzer (Technicon Instruments, Tarrytown, N.Y.), utilizing the Sigma Total Cholesterol Diagnostic Kit (Sigma Chemical Co., St. Louis, Mo., Cat#352). HDL cholesterol was determined by heparin sulfate precipitation of Apolipoprotein B containing lipoproteins. The supernatant was than assayed for cholesterol as indicated above. LDL cholesterol was determined by subtraction of HDL cholesterol from total serum cholesterol.

After the first five weeks of fat enriched diet, the light-:dark cycle of the animal room was shifted from a 7 AM:7 PM cycle to a 2 AM:2 PM cycles in two stages, two weeks in duration. The animals remained on the 2 AM:2 PM light:dark cycle for the remaining five weeks of this study to allow entrainment of peak cholesterol and bile acid biosynthesis to the new mid-dark cycle. Plasma cholesterol was measured, as previously described, at weeks 8, 11 and 13. Feces were collected from the hamsters during the last three days of the study, ground, pooled and frozen at −20° C. until extracted for fecal bile acid analysis.

During week 14, one half of the animals in each treatment group were sacrificed on two successive days at the middle of the dark cycle (6 PM:10 PM). The animals were anesthetized with sodium pentobarbital (0.1 ml/100 gram body weight) via intraperitoneal injection. The abdominal cavity of the anesthetized animal was opened and gall bladder bile was aspirated with a 27 gauge needle. Bile from animals in the same treatment group was pooled and frozen in liquid nitrogen. The liver was then clamped at the hilum with a hemostat and excised. The livers were split into three pieces and frozen in liquid nitrogen. The animal was then exsanguinated via the abdominal aorta, the blood was transferred to a heparin containing tube and chilled on ice until separation of the plasma by centrifugation. Plasma was then stored at 5° C. until analyzed for cholesterol content. The animals were then terminated by puncturing the diaphragm to induce pneumothorax.

The animal was then perfused via the heart with 4% formalin in phosphate buffered saline for 20 minutes. The aorta was then excised and placed in fixative until further analysis.

Bile acids in gall bladder bile were analyzed by HPLC; fecal extracts were analyzed by gas chromatography. HMG-CoA Reductase activity was analyzed in both liver and enterocytes. Cholesterol 7α-hydroxylase activity was analyzed in the liver. Total, free and esterified cholesterol content in the liver was determined. The aortas were examined for extent of surface area covered by fatty streaks.

Experimental Results

Figure 2:
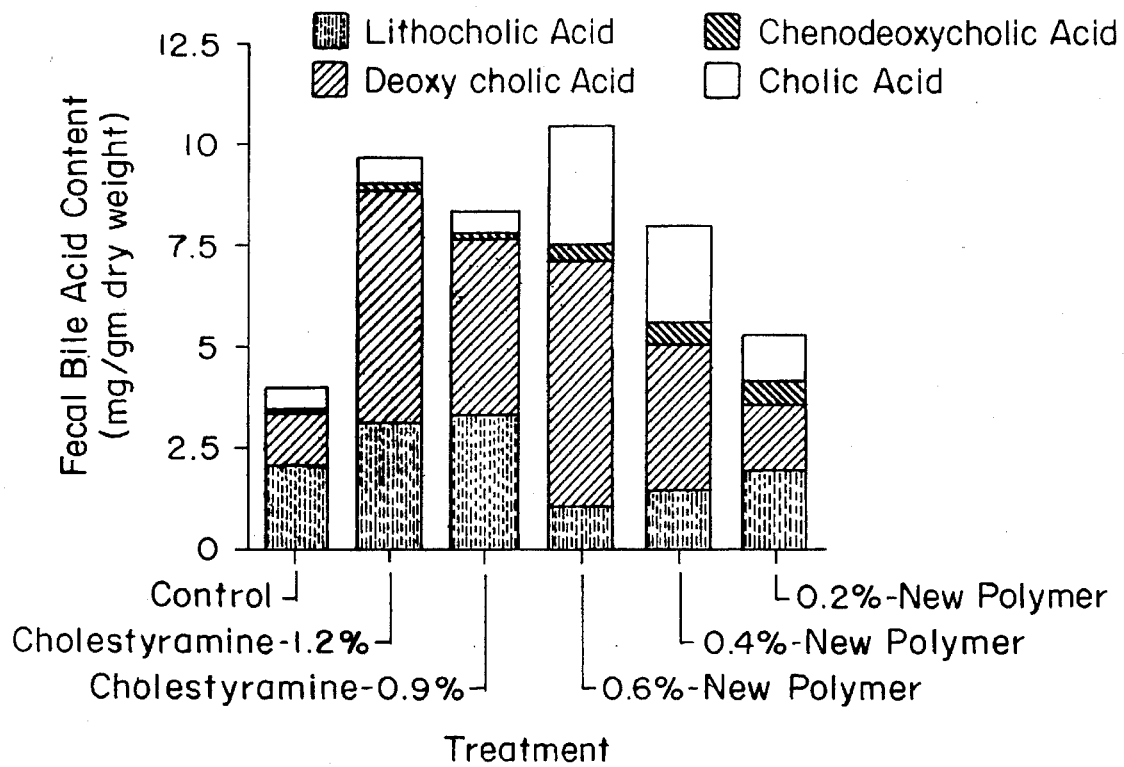
FIG. 2 is a bar graph of the comparative effect of the polymer of the invention and cholestyramine on fecal bile acid content in hamsters fed a high fat diet for 14 weeks.
Figure 3:
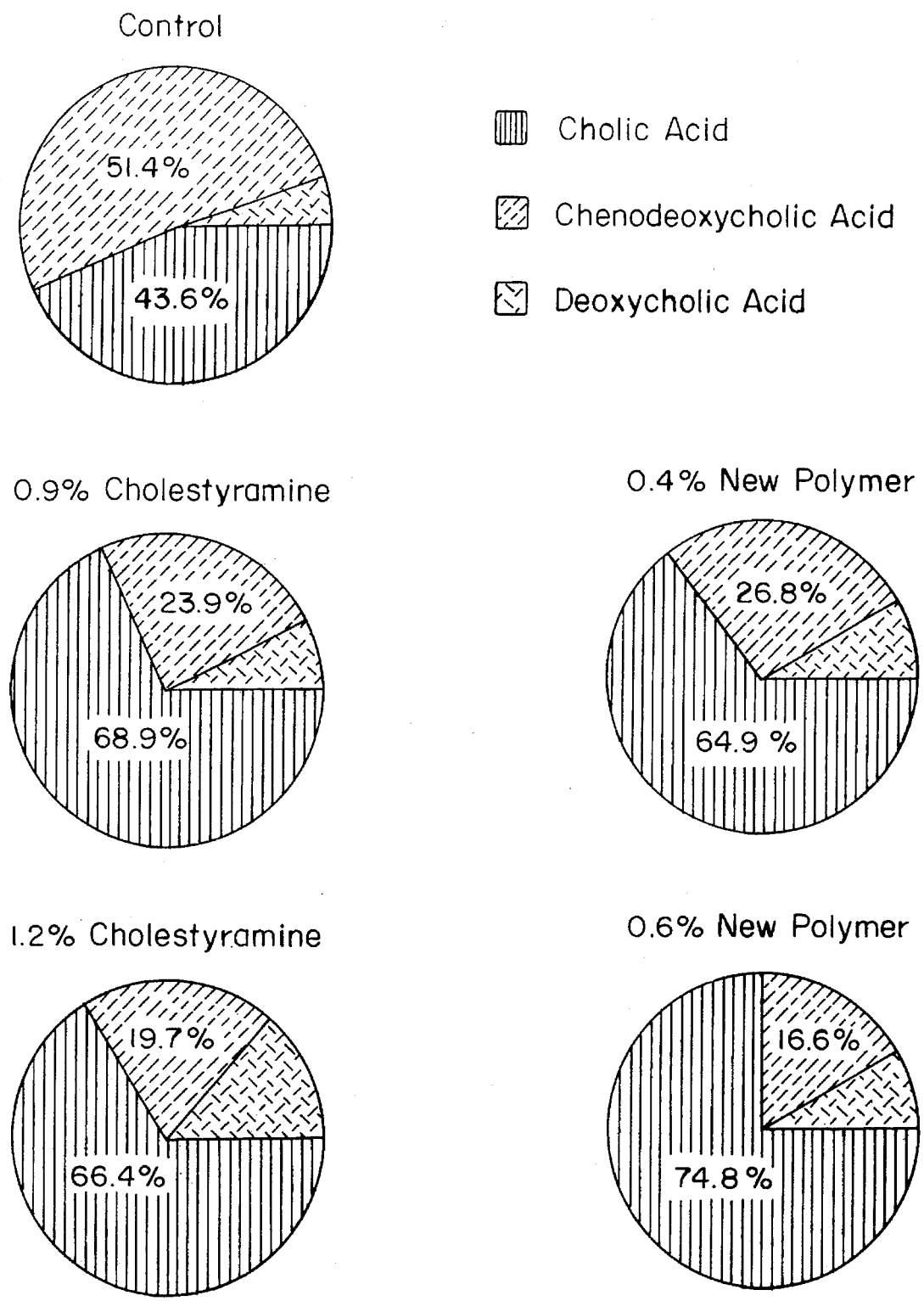
FIG. 3 is a graphical representation of the effect of bile acid sequestrants on gall bladder bile acid profile in fat fed hamsters.

Plasma total and nonHDL (LDL+VLDL) cholesterol decreased in animals treated with the bile acid sequestrants at 14 weeks, as shown in FIG. 1. The polymer formed by the method of Example 6 (hereinafter the "new polymer") was approximately three times more potent as a lipid lowering agent than cholestyramine since 0.4% of the new polymer provided similar lipid lowering effects at 1.2% cholestyramine. Animals treated with 0.6% new polymer have significantly lower cholesterol than cholestyramine treated animals. The added potency in lipid lowering activity is surprising in view of data indicating that fecal bile acid mass in 1.2% cholestyramine treated animals was similar to that of 0.6% new polymer treated animals, as shown in FIG. 2. Similarly, the lipid lowering effect of 0.4% new polymer was greater than that of 0.9% cholestyramine despite similar bile acid mass excretions. Treatment of fat fed hamsters with bile acid sequestrants for 14 weeks alters gall bladder bile acid content, as shown in FIG. 3. Cholic acid content rose to almost 75% in 0.6% new polymer treated animals, while chenodeoxycholic acid content declined below 17%. As a result, high affinity binding of cholic acid became particularly advantageous. In contrast, similar changes were observed for 1.2% cholestyramine treated animals but the weak binding of cholic acid by this bile acid sequestrant limits efficacy.

Figure 4:
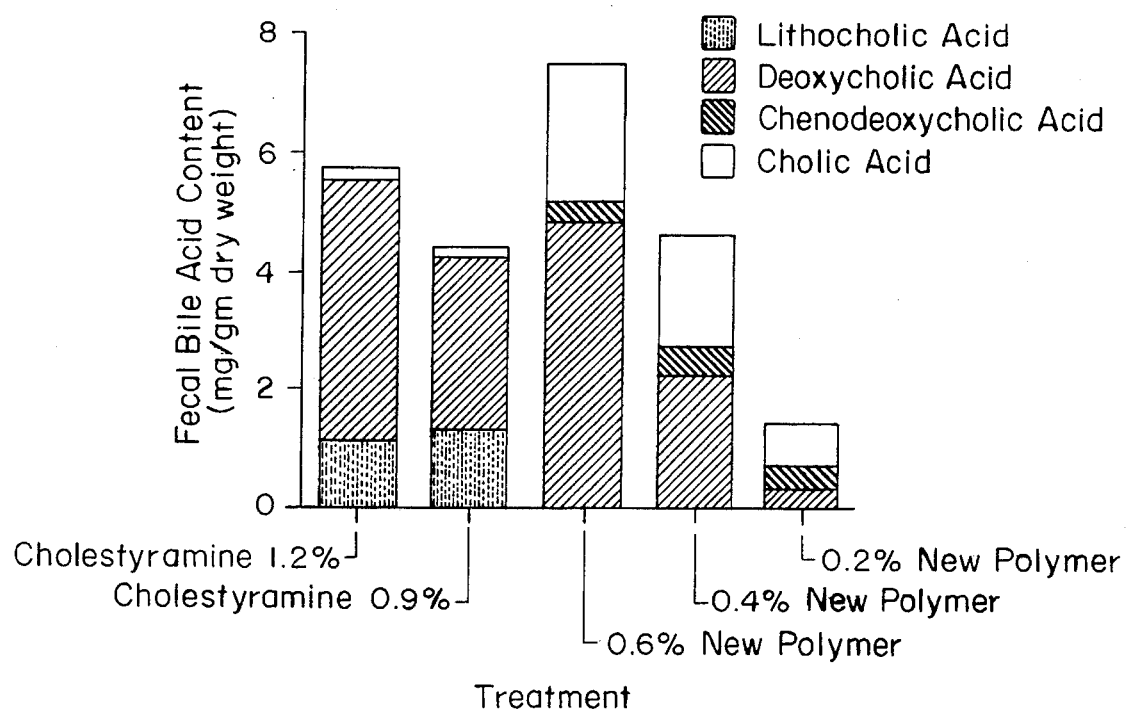
FIG. 4 is a bar graph of the comparative increase in fecal bile acid excretion by type in hamsters fed a high fat diet with the polymer of the invention and cholestyramine for 14 weeks.

The effect of the various sequestrant on fecal bile acid excretion is demonstrated in FIG. 4. In the figure, the data is presented as the difference between fecal bile acid mass in control animals and those of drug treated animals. These data demonstrate that the new polymer results in 500% increases in fecal excretion of both cholic and chenodeoxycholic acids. The increased excretion of chenodeoxycholic acid is particularly interesting since the content of this bile acid in gall bladder bile was decreased by 68%.

Figure 5:
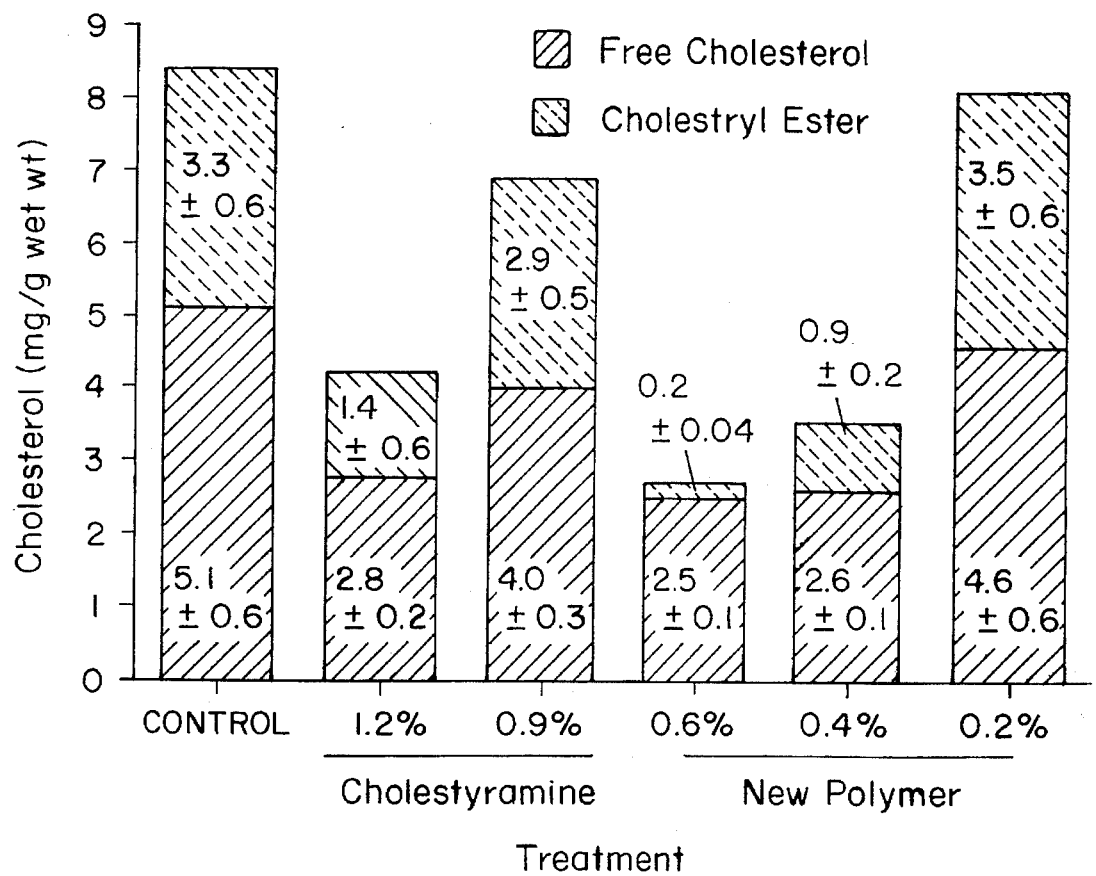
FIG. 5 is a bar graph of the comparative effects of cholestyramine and the polymer of the invention on liver free and esterified cholesterol.
Figure 6:
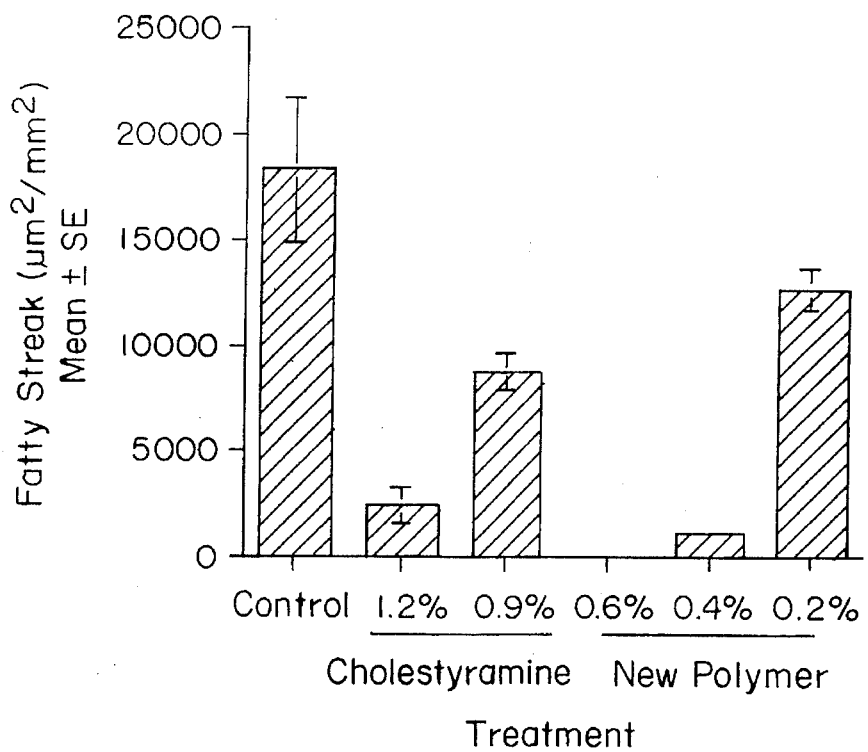
FIG. 6 is a bar graph of the comparative effect of the polymer of the invention and cholestyramine on aortic fatty streak area.

The difference in binding profile of new polymer appeared to effect liver and aortic lipid mass to a greater extent that plasma lipids. As shown in FIG. 5, 0.6% and 0.4% new polymer reduced liver cholesteryl ester content by 92% and 73%, respectively. In contrast, 1.2% cholestyramine reduced liver cholesteryl ester content by 58%. The effects on aortic fatty streak formation were similar. No fatty streak formation was observed with 0.6% new polymer, while the extent of fatty streak formation with 0.4% new polymer was approximately half of that observed with cholestyramine, despite comparable plasma cholesterol levels.

Figure 7:
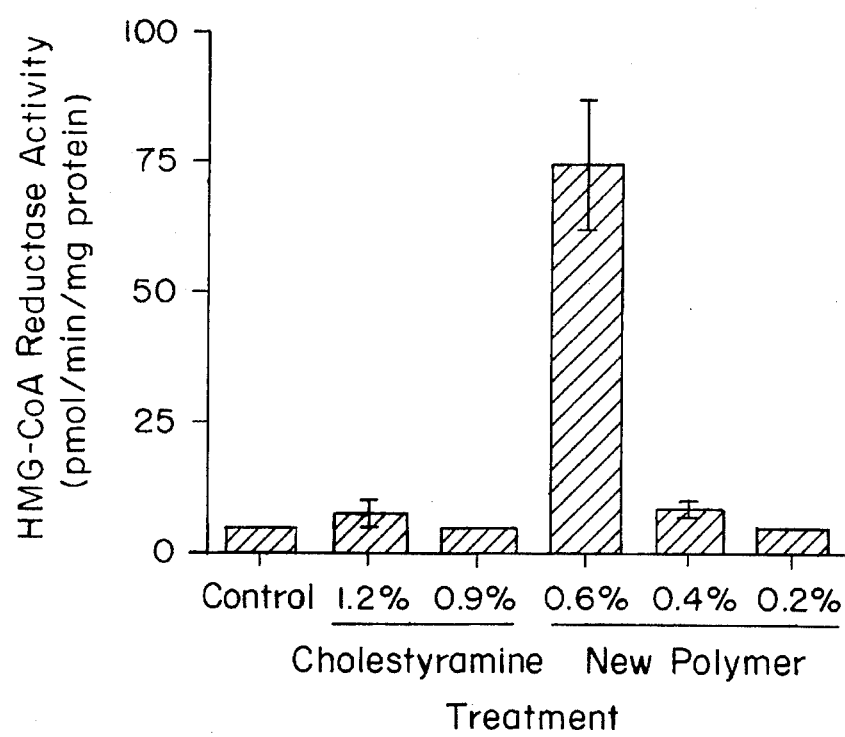
FIG. 7 is a bar graph of the comparative effect of the polymer of the invention and cholestyramine on liver HMG CoA reductase activity.
Figure 8:
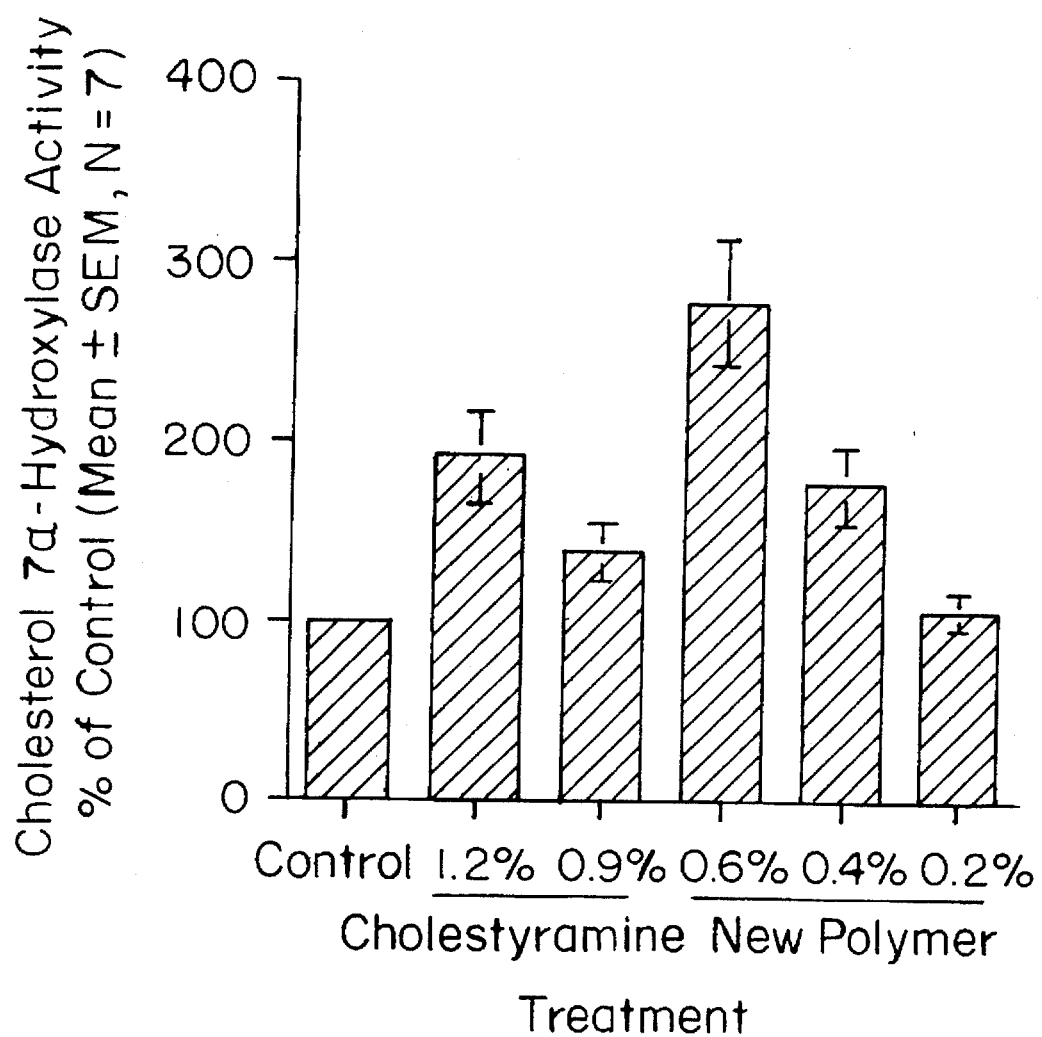
FIG. 8 is a bar graph of the comparative effect of the polymer of the invention and cholestyramine on hepatic cholesterol $7\alpha$-hydroxylase activity.

The effect of new polymer of indication on HMG CoA-Reductase, the rate limiting enzyme in cholesterol biosynthesis, and in cholesterol 7α-hydroxylase, the rate limiting enzyme on bile acid synthesis, shown in FIGS. 7 and 8, support the unexpected finding that the physiological response to the new polymer exceeded the lipid lowering and bile acid mass excretion. We conclude that high affinity sequestration of primary, conjugated bile acids elicits a plasma lipid lowering beyond the mass effect of fecal bile acid excretion. Further, we conclude that the enhanced hepatic and aortic lipid lowering effects support the inference of biological importance conferred to the conjugated, primary bile acids by the preferential reabsorption demonstrated by the energy dependent, ileal bile acid transport system.

EXAMPLE 8

In vitro Binding of Conjugated Primary Bile Acids

Solutions of the bile acids to be tested (glycocholic acid and glycochenodeoxycholic acid) were prepared by dissolving them, individually, at a concentration of 15 mmolar in buffer (100 mM BES and 160 mM NaCl, pH 7.0). Buffer without bile acid were also prepared.

Polymer samples prepared by the method of Example 3 were weighed (10 mg) into seven individual, 15 mL, capped test tubes. Buffer and bile acid buffer solution were added such that concentrations of bile acid from 0.25 mM to 15 mM were obtained. The tubes were incubated at room temperature for at least 12 hours and the polymer plus bound bile acid were removed from the supernatant liquid via filtration.

The supernatant liquid was analyzed by HPLC to determine the amount of unbound bile acid; the bound bile acid was calculated by difference. The amount of bound and unbound bile acid were graphed to yield isotherms of the form shown in FIG. 9.

Figure 9:
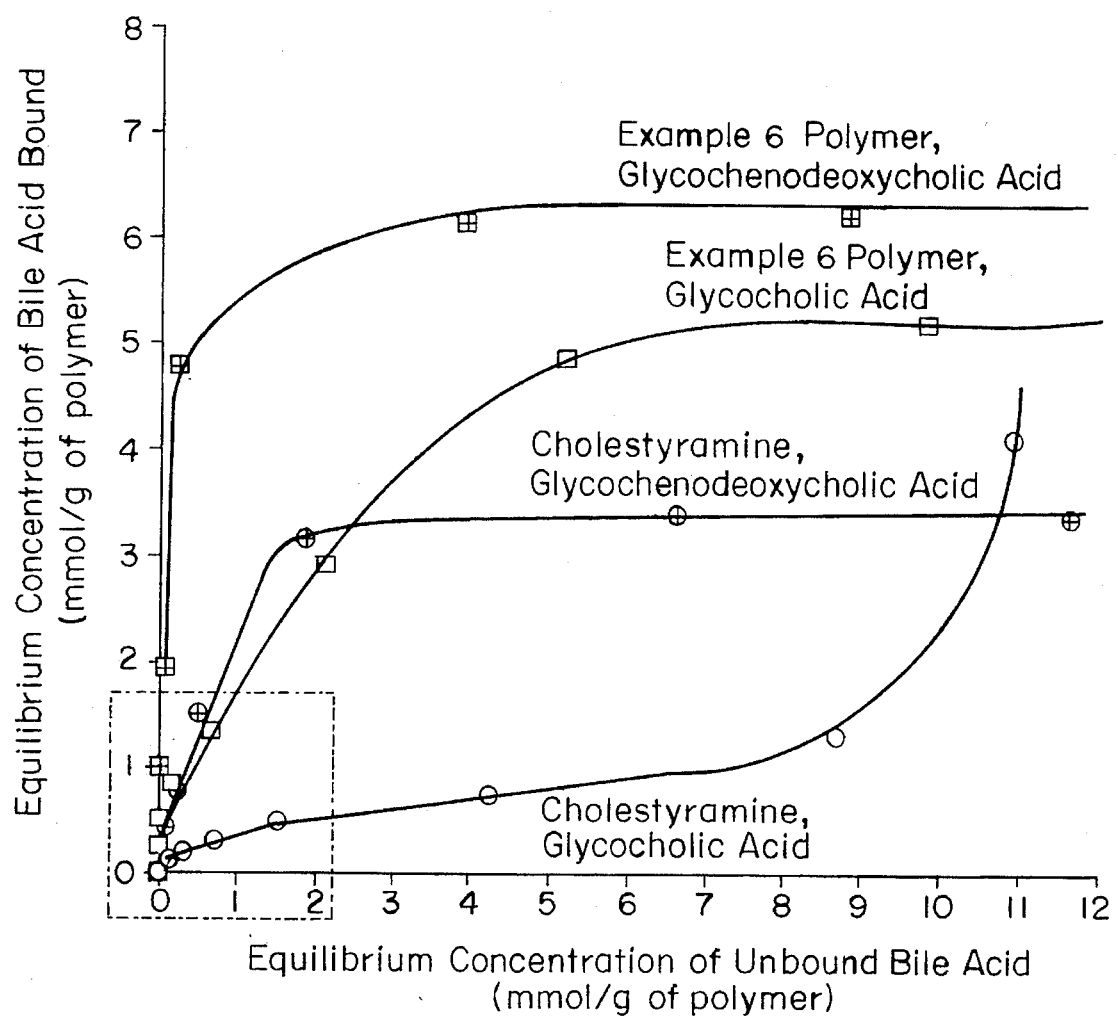
FIG. 9 is a plot of bile acid isotherms comparing the polymer of the invention with cholestyramine following the in vitro experiment, detailed in Example 8.
Figure 10:
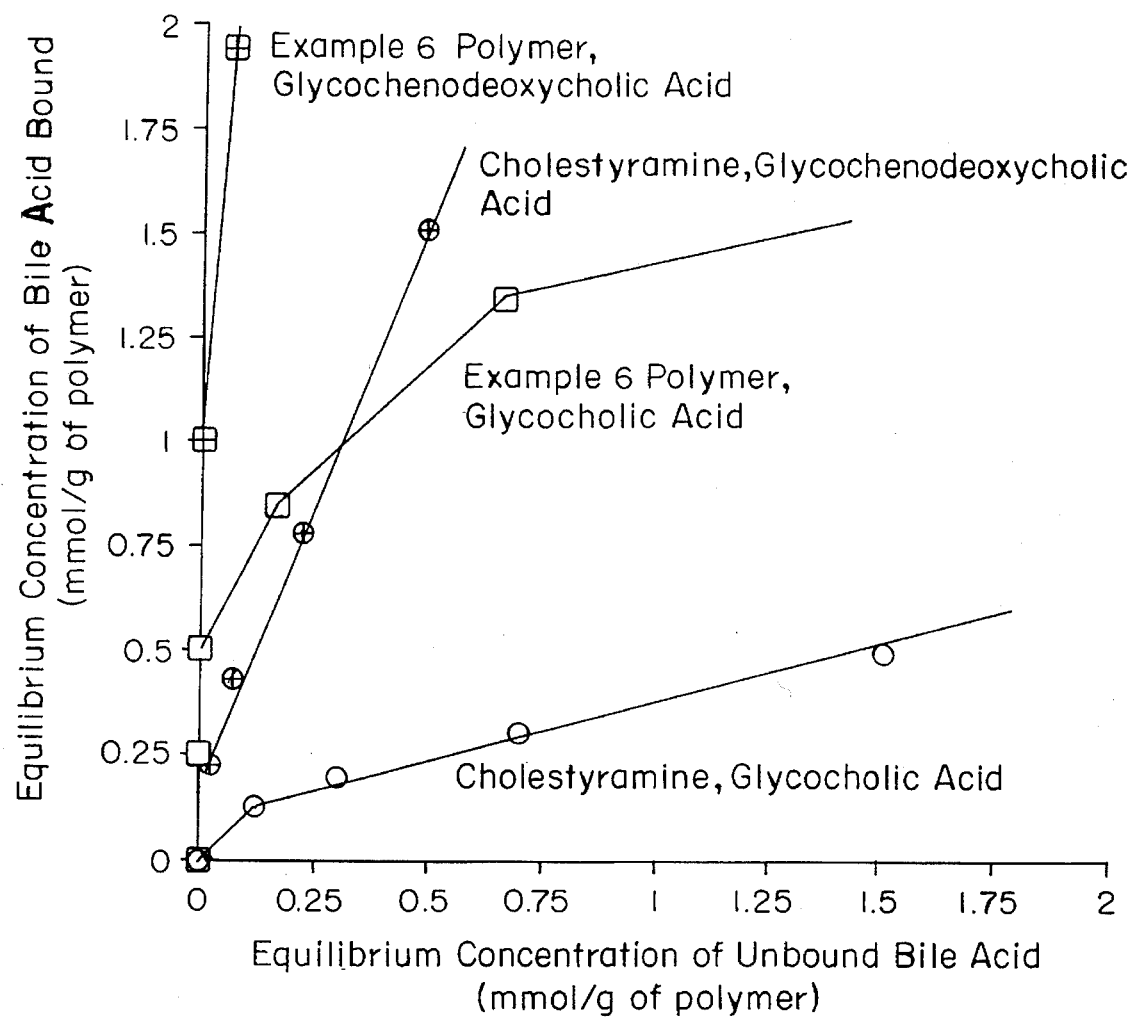
FIG. 10 is an enlargement of a 0–2 mM portion of the plot of FIG. 9, showing very high affinity binding of glycocholic acid and glycochenodeoxycholic acid by the polymer of the invention.

FIGS. 4, 9 and 10 showed that the amine polymer of the invention bound conjugated primary bile acids, cholic and chenodeoxycholic acids, with sufficient affinity as to be essentially irreversible, thereby preventing both active transport of these bile acids, and bacterial deconjugation and dehydroxylation that normally occurs in the large intestine. Further, it is believed that this high-affinity binding, which in effect removed significant portions of conjugated cholic and chenodeoxycholic acids from the jejunal and ileal bile acids pool, and resulted in enhanced lipid lowering and antiatherosclerotic effects.

Equivalents

Those skilled in the art will recognize, or be able to ascertain using no more than routine experimentation, many equivalents to specific embodiments of the invention described specifically herein. Such equivalents are intended to be encompassed in the scope of the following claims.

We claim:

1. A method for binding bile salts in a mammal, comprising the step of orally administering to the mammal a therapeutic amount of an amine polymer having a first substituent, bound to a first amine of the amine polymer, that includes a hydrophobic aliphatic moiety, and a second substituent, bound to a second amine of the amine polymer, that includes an aliphatic quaternary amine-containing moiety.

2. A method for reducing blood cholesterol in a mammal, comprising the step of orally administering to the mammal a therapeutic amount of an amine polymer having a first substituent, bound to a first amine of the amine polymer, that includes a hydrophobic aliphatic moiety, and a second substituent, bound to a second amine of the amine polymer, that includes an aliphatic quaternary amine-containing moiety.

3. A method for treating atherosclerosis in a mammal, comprising the step of orally administering to the mammal a therapeutic amount of an amine polymer having a first substituent, bound to a first amine of the amine polymer, that includes a hydrophobic aliphatic moiety, and a second substituent, bound to a second amine of the amine polymer that includes an aliphatic quaternary amine-containing moiety.

4. A method for treating hypercholesterolemia in a mammal, comprising the step of orally administering to the mammal a therapeutic amount of an amine polymer having a first substituent, bound to a first amine of the amine polymer, that includes a hydrophobic aliphatic moiety, and a second substituent, bound to a second amine of the amine polymer, that includes an aliphatic quaternary amine-containing moiety.

5. The method of claim 1, wherein said amine polymer is cross-linked.

6. The method of claim 5, wherein said amine polymer is cross-linked prior to substitution by said first and second substituents.

7. The method of claim 6, wherein said amine polymer comprises a crosslinking moiety that is present in a range of between about 0.5 and twenty percent of amines of the polymer.

8. The method of claim 7, wherein the crosslinking moiety is present in a range of between about 0.5 and six percent of amines of the polymer.

9. The method of claim 7, wherein the hydrophobic moiety is an alkyl group of at least six carbons.

10. The method of claim 9, wherein the hydrophobic moiety is an alkyl group of between about eight and twelve carbons.

11. The method of claim 10, wherein the hydrophobic moiety is an alkyl group of about ten carbons.

12. The method of claim 9, wherein the quaternary amine-containing moiety is an alkyltrialkyl ammonium.

13. The method of claim 12, wherein said alkyltrialkyl ammonium is an alkyltrimethyl ammonium wherein said alkyl has between about two and twelve carbons.

14. The method of claim 13, wherein said alkyl is a hexyl group.

15. The method of claim 13, wherein said alkyl is an octyl group.

16. The method of claim 13, wherein said alkyl is a decyl group.

17. The method of claim 12, wherein said amine polymer is poly(ethylenimine).

18. The method of claim 12, wherein said amine polymer has a hydrocarbon backbone.

19. The method of claim 18, wherein said amine polymer is poly(vinylamine).

20. The method of claim 17, wherein said amine polymer is poly(allylamine).

21. The method of claim 20, wherein the hydrophobic moiety of said first amino substituent is a decyl group.

22. The method of claim 21, wherein the quaternary amine-containing moiety of said second amino substituent is hexyltrimethylammonium.

23. The method of claim 22, wherein the amine polymer is crosslinked by a crosslinking moiety that is present in a range of between about 0.5 and twenty percent of the amines of the polymer.

24. The method of claim 23, wherein said crosslinking moiety is epichlorohydrin.

25. A method of reducing cholesterol in a mammal comprising the step of orally administering to the mammal a therapeutic amount of a crosslinked poly(allylamine) polymer comprising:

a) a first substituent, bound to an amine of the amine polymer, that includes a hydrophobic decyl moiety; and b) a second substituent, bound to an amine of the amine polymer that includes hexyltrimethylammonium, wherein the poly(allylamine) is crosslinked by epichlorohydrin, prior to substitution by (a) and (b), and said epichlorohydrin is present in a range of between about 0.5 and twenty mole percent of the amines of the poly(allylamine).

* * * * *

UNITED STATES PATENT AND TRADEMARK OFFICE
CERTIFICATE OF CORRECTION

PATENT NO. : 5,607,669
DATED : March 4, 1997
INVENTOR(S) : W. Harry Mandeville, III and Stephen R. Holmes-Farley It is certified that error appears in the above-indentified patent and that said Letters Patent is hereby corrected as shown below:

Col. 12, line 41 in Claim 20 delete "17" and insert --18-- therefor.

Signed and Sealed this

Fifteenth Day of July, 1997

Attest:

BRUCE LEHMAN

Attesting Officer

Commissioner of Patents and Trademarks